June 24, 1941. W. KORDES Plant Pat. 475
ROSE PLANT
Filed Feb. 10, 1941
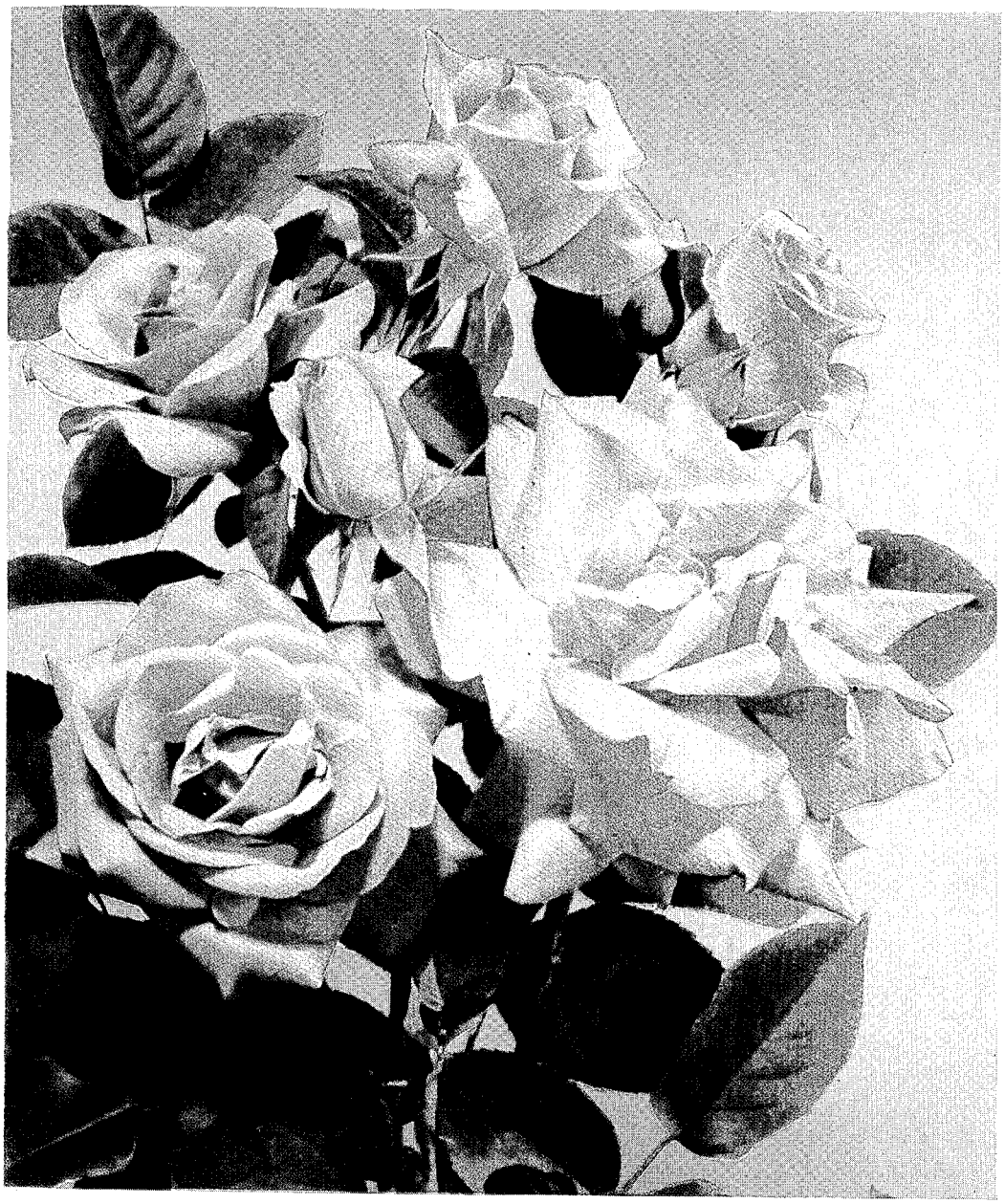
Inventor
Wilhelm Kordes
By Robb & Robb
Attorneys.

Patented June 24, 1941

UNITED STATES PATENT OFFICE

475

ROSE PLANT

Wilhelm Kordes, Holstein, Germany, assignor to Jackson & Perkins Company, Newark, N. Y.

Application February 10, 1941, Serial No. 378,265

1 Claim. (Cl. 47—61)

The present invention relates to a new and distinct variety of rose plant of the large flowered polyantha type.

This new rose has many points of distinctiveness among which may be noted, abundance of foliage and heavy texture thereof, and its freedom of flowering, together with the large size of the blooms and continuity of blooming, all of which impart particular value to this variety for decorative garden use.

The novelty of color of the flowers is of primary importance, due to the peculiar lightening of color of the lower third of the petals which gives the flower an interesting luminosity, the general tonality ranging from Carmine to Pomegranate Purple and persisting throughout all of the stages of blooming.

The foregoing distinctions are more specifically referred to in the following detailed description, wherein all color terminology accords with Ridgway's Color Standard:

Parentage: Seedling.

*Seed parent.*—Dance of Joy.

*Pollen parent.*—E. G. Hill × Catherine Kordes.

Classification:

*Botanic.*—Large flowered polyantha.

*Commercial.*—Floribunda.

*Flower*

Blooming habit: (Observations made in fields and gardens of Jackson & Perkins Company, Newark, New York, in the afternoon of June 21, 1940.)

*Recurrent.*—Continuous.

Bud:

*Size.*—Medium.

*Form.*—Pointed. Is not affected by wet or hot weather.

*Color.*—When sepals first divide—Oxblood Red, Plate I. When petals begin to unfurl—Pomegranate Purple, Plate XII. When half blown: inside of petals—between Pomegranate Purple, Plate XII, and Rose Red, Plate XII; reverse of petals—between Carmine, Plate I, and Tyrian Rose, Plate XII.

*Sepals.*—Serrated, branched. Curl back when petals unfold. *Color*: inside—Apple Green, Plate XVII; outside—Light Cress Green, Plate XXXI.

*Calyx.*—*Shape*—apple. *Size*—small. *Aspect*—smooth. *Color*—Cress Green, Plate XXXI.

*Peduncle.*—*Length*—short. *Aspect*—rough. *Color*—Oil Green, Plate V. *Strength*—stiff, heavy.

*Opening.*—Bud opens well. Is not affected by adverse conditions.

Bloom:

*Size.*—Large. Average size when fully expanded—4–4½ inches.

*Borne.*—In clusters, irregular.

*Stems.*—Medium length; strong.

*Form.*—When first open—flat. *Permanence*—retains its form to the end.

*Petalage.*—Double (full but open center). Number of petals under normal conditions—24–25.

*Color.*—Center of flower—between Carmine, Plate I, and Pomegranate Purple, Plate XII. Outer petals—between Carmine, Plate I, and Pomegranate Purple, Plate XII. Base of petals (aiglet)—Straw Yellow, Plate XVI. Inside of petals; upper two-thirds—between Carmine, Plate I, and Pomegranate Purple, Plate XII; lower third—lightening to Tyrian Rose, Plate XII. Reverse of petals—between Pomegranate Purple, Plate XII, and Rose Red, Plate XII. General tonality from a distance—between Carmine, Plate I, and Pomegranate Purple, Plate XII.

*Discoloration.*—General tonality at end of first day—Carmine, Plate I, to Pomegranate Purple, Plate XII. Second day—Carmine, Plate I, to Pomegranate Purple, Plate XII. Third day— leaning towards Pomegranate Purple, Plate XII.

Petals:

*Texture.*—Leathery. Is not affected by wet or hot weather.

*Appearance.* — Inside — velvety. Outside — shiny.

*Form.*—Oval.

*Arrangement.*—Imbricated (regularly arranged shingle-like). *Petaloids in center*—few, small.

*Persistence.*—Drop off cleanly.

*Fragrance.*—Moderate. *Nature*—average hybrid tea scent.

*Lasting quality.*—On the plant and as cut flower—long.

Genital organs:

*Stamens, anthers.*—*Size*—medium; many. *Color*—Light Cadmium, Plate IV. *Arrangement*—regular around styles.

*Stamens, filaments (threads).*—Medium length. *Color*—Jasper Red, Plate XIII.

*Pollen.*—Cadmium Yellow, Plate III.

*Styles.*—Bunched; medium length; thin.

*Stigmas.*—Pinard Yellow, Plate IV.

*Ovaries.*—All enclosed in calyx.

*Plant*

Form: Bush.

Growth: Vigorous; upright; compact.

Foliage: 5–7 leaflets.

*Size.*—Medium.

*Quantity.*—Abundant.

*Color.*—*New foliage:* upper side—Hessian Brown, Plate XIII; under side—Van Dyke Red, Plate XIII. *Old foliage:* upper side—Cress Green, Plate XXI; under side—Light Cress Green, Plate XXXI.

*Shape.*—Oval pointed.

*Texture.*—Upper side—leathery. Under side—rough. *Ribs and veins*—prominent.

*Edge.*—Serrated (saw toothed).

*Serrations.*—Single; small.

*Rachis.*—*Color*—Cress Green, Plate XXXI. Under side—hooks.

*Stipules.*—Medium length; bearded.

*Disease resistance.*—Resistant.

Wood:

*New wood.*—*Color*—Brick Red, Plate XIII. *Bark*—smooth, rough.

*Old wood.*—*Color*—Cress Green, Plate XXXI. *Bark*—smooth.

Thorns (thorns are divided into thorns, prickles and short needles):

*Thorns.*—*Quantity*—on main stalks from base—many. On laterals from stalk—many. *Form*—flat base; medium length, hooked downward. *Color when young*—Lettuce Green, Plate V. *Position*—irregular.

*Prickles.*—*Quantity*—on main stalks—few. *Color*—Lettuce Green, Plate V.

*Short needles.*—*Quantity*—on main stalks—none. On laterals—none.

Asexual reproduction of this new rose shows that the noted distinctive features are fixed.

I claim:

A new and distinct variety of rose plant of the floribunda class, characterized as to novelty by its abundance of foliage of heavy texture, freedom and continuity of blooming, and the size, shape, and color of its flowers, substantially as shown and described.

WILHELM KORDES.